United States Patent [19]
Jones et al.

[11] Patent Number: 5,782,792
[45] Date of Patent: Jul. 21, 1998

[54] METHOD FOR TREATMENT OF RHEUMATOID ARTHRITIS

[75] Inventors: Frank R. Jones, Edmonds; Harry W. Snyder, Jr.; Joseph P. Balint, Jr., both of Seattle, all of Wash.

[73] Assignee: Cypress Bioscience, Inc., San Diego, Calif.

[21] Appl. No.: 353,946

[22] Filed: Dec. 12, 1994

Related U.S. Application Data

[63] Continuation of Ser. No. 878,636, May 5, 1992, abandoned, which is a continuation-in-part of Ser. No. 453,236, Dec. 14, 1989, abandoned, which is a continuation of Ser. No. 344,463, Apr. 26, 1989, abandoned, which is a continuation of Ser. No. 934,272, Nov. 21, 1986, abandoned.

[51] Int. Cl.[6] ............................................... A61M 37/00
[52] U.S. Cl. .................. 604/5; 604/4; 424/529; 210/195.2
[58] Field of Search ............... 604/4–6; 435/269; 424/529, 530; 210/638, 632, 264, 195.2, 434; 514/2, 8, 12

[56] References Cited

U.S. PATENT DOCUMENTS

| | | | |
|---|---|---|---|
| 4,381,004 | 4/1983 | Babb | 604/5 |
| 4,464,165 | 8/1984 | Pollard, Jr. | 604/5 |
| 4,551,435 | 11/1985 | Liberti . | |
| 4,614,513 | 9/1986 | Bensinger . | |
| 4,627,915 | 12/1986 | Kuroda et al. | 210/195.2 |
| 4,681,870 | 7/1987 | Balint . | |
| 4,685,900 | 8/1987 | Honard . | |
| 4,714,556 | 12/1987 | Ambrus et al. | 210/638 |
| 5,356,374 | 10/1994 | Hogan et al. | 604/4 |

FOREIGN PATENT DOCUMENTS

| | | |
|---|---|---|
| 0269279 | 6/1988 | European Pat. Off. . |
| 57-77624 | 5/1982 | Japan ............... A61K 39/44 |

OTHER PUBLICATIONS

T. Agishi et al., *Screening of Immunoadsorbents*, Jinko Zoki, vol. 9; p. 264 (1980).

C. Freiburghaus et al., *A Summary of Five Years' Clinical Experience with Extensive Removal of Immunoglobulins*, Plasma Therapy & Transfusion Technology; vol.7, No.4; pp. 545–550 (Dec. 1986).

P. Geborek et al., *Modified Immunosuppression After Apheresis and I.V. Gammaglobulin in Severe Rheumatoid Arthritis*, Innov. Tech. Biol. Med.; vol. 6, No. 2; pp. 236–241 (Feb. 13, 1985).

L. D. Johnson et al., *Chromatographic Behavior of Histones on Sephadex and Carboxymethylcellulose*, Canadian Journal of Biochemistry, vol. 42; pp. 795–811 (1964).

H. M. Lazarus et al., *Selective In Vivo Removal of Rheumatoid Factor by an Extracorporeal Treatment Device in Rheumatoid Arthritis Patients*, Transfusion, vol. 31, No. 2; pp. 122–128 (1991).

D. Terman et al., *Extensive Necrosis of Spontaneous Canine Mammary Adenocarcinoma After Extracorporeal Perfusion Over Staphylococcus Aureus Cowans I |I. Description of Acute Tumoricidal Response: Morphologic, Hostologic, Immunohistochemical, Immunoglogic, and Serologic Findings[1]*, The Journal of Immunology, vol. 124, No. 2; pp. 795–805 (Feb. 1980).

(List continued on next page.)

*Primary Examiner*—Michael Powell Buiz
*Assistant Examiner*—A. T. Nguyen
*Attorney, Agent, or Firm*—Cooley Godward LLP

[57] ABSTRACT

Rheumatoid arthritis is treated by the extra corporeal removal of IgG and IgG-containing circulating immune complexes from the patient's blood. Removal is preferably accomplished by exposing the blood or blood plasma to a protein A immunoadsorbent which binds to IgG-containing immune complexes with high affinity.

13 Claims, 4 Drawing Sheets

OTHER PUBLICATIONS

D. Terman, *Preliminary Observations of the Effects of Breast Adenocarcinoma of Plasma Perfused Over Immobilized Protein A*, The New England Journal of Medicine, vol. 305, No. 20; pp. 1195–1200 (Nov. 12, 1981).

Z. Yamazaki et al., *Extracorporeal Immunoadsorption with IM–PH or IM–TR Column*, Biomat., Art. Cells., Art. Org., vol. 17, No. 2; pp. 117–124 (1989).

T. Agishi et al., *Screening of Immunoadsorbents*, Jinko Zoki, vol. 9; p. 264 (1980).

C. Freiburghaus et al., *A Summary of Five Years' Clinical Experience with Extensive Removal of Immunoglobulins*, Plasma Therapy & Transfusion Technology; vol. 7, No.4; pp. 545–550 (1986).

D. Kiprov et al., *Extracorporeal Perfusion of Plasma over Immobilized Protein A in a Patient with Kaposi's Sarcoma and Acquired Immunodeficiency*, Journal of Biological Response Modifiers, vol. 3; pp. 341–346 (1984).

F. Roy MacKintosh et al., *Treatment of Advanced Malignancy with Plasma Perfused Over Staphylococcal Protein A*, The Western Journal of Medicine, vol. 139; pp. 38–40 (1983).

A.K. Schröder et al., *Binding of IgM Rheumatoid Factor to Group A, C and G Streptococci with IgG Fc Receptors*, Int. Archs Allergy appl. Immun., vol. 80; pp. 52–56 (1986).

Korec et al. (1984) J. Biol. Resp. Mod. 3:330–335.

Terman et al. (1979) The Lancet, Oct. 20 pp. 824–826.

Braude et al., 'Specific Microbial Agents of Disease, Aerobic Bacterial or Facultatively Anaerobic Bacteria', Infectious Diseases and Medical Microbiology, 2nd Ed., pp. 236–237 (1986).

Stites et al., Basic and Clinical Immunology, 7th Ed., pp. 233 and 443–444 (1991).

Schroder et al, "Bindings of IgM Rheumatoid Factor to Group A, C, and G Streptococci with IgG Fc Receptors", Int. Archs Allergy appl. Immun. 80: 52–56 (1986).

MacKintosh et al, "Treatment of Advanced Malignancy with Plasma Perfused Over Staphylococcal Protein A", *The Western Journal of Medicine*, vol. 139, No. 1, pp. 36–40 (1983).

Kiprov et al, "Extracorporeal Perfusion of Plasma over Immobilized Protein A in Patient with Kaposi's Sarcoma & Acq'd Immunodeficiency", *Journal of Biological Response Modifiers*, vol. 3, pp. 341–346 (1984).

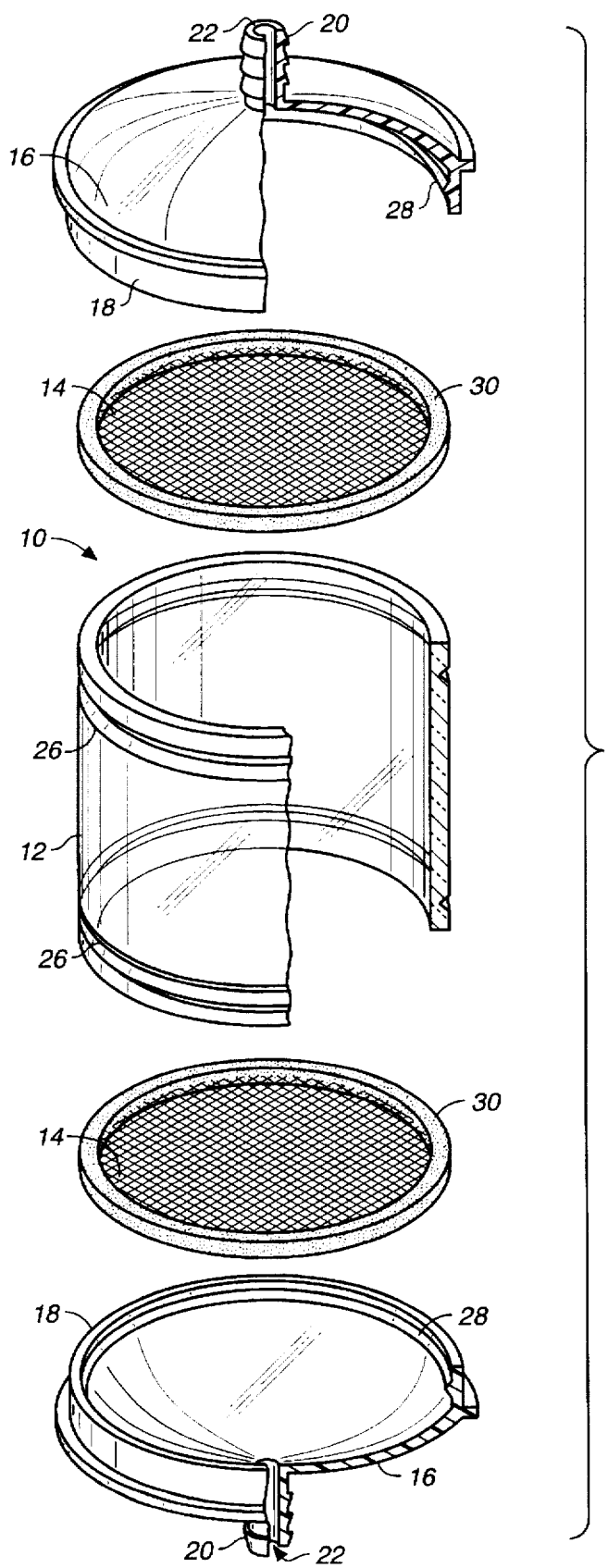
FIG._1

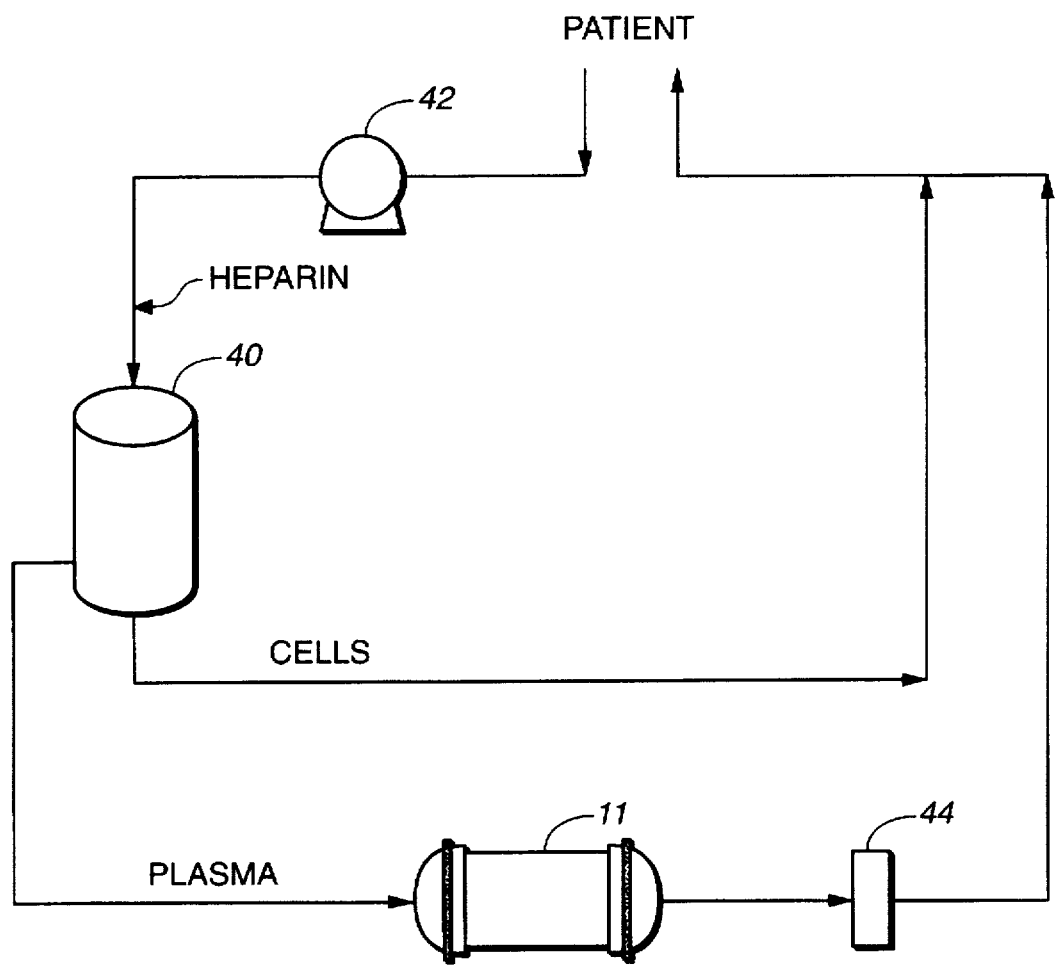
FIG._2

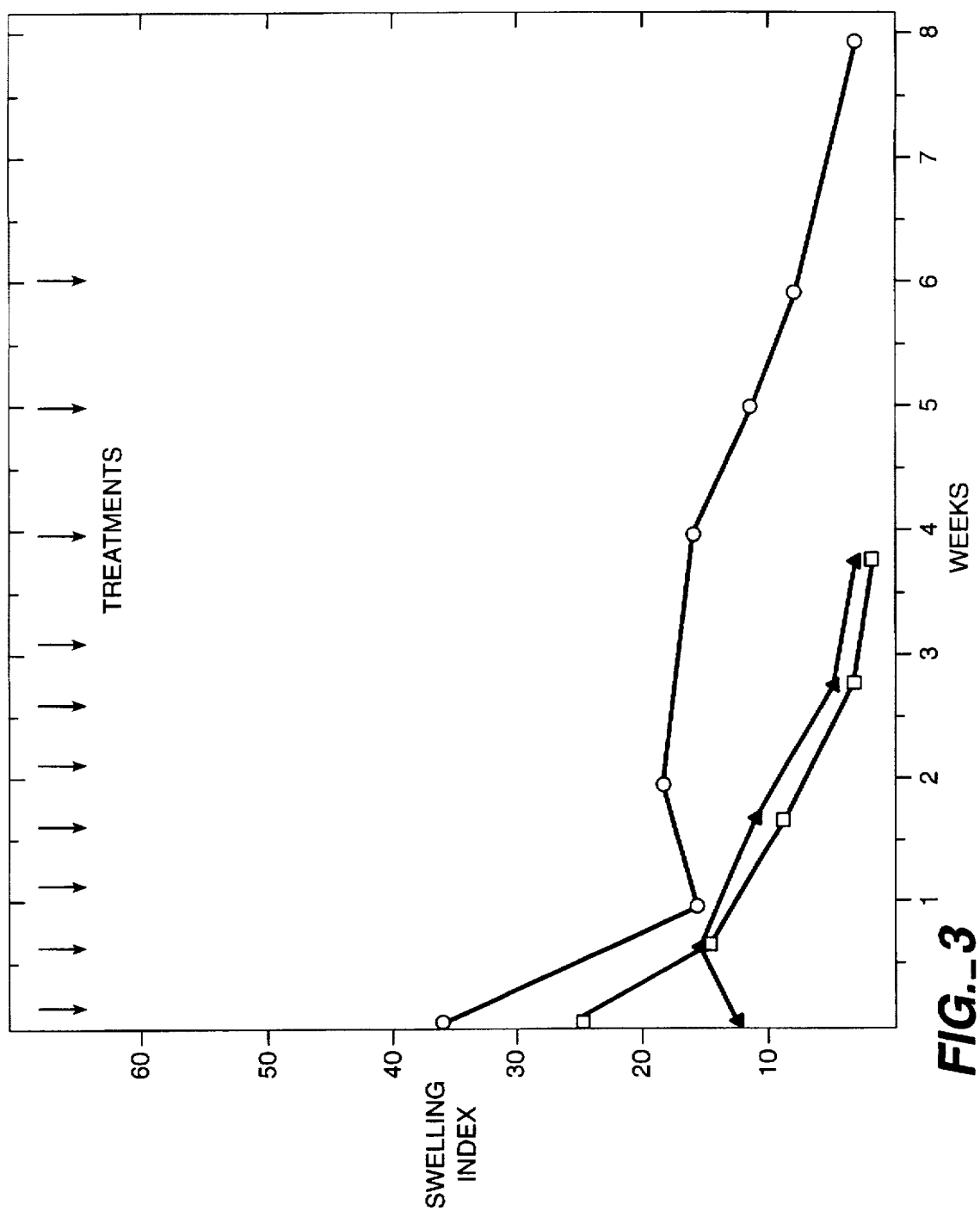
FIG._3

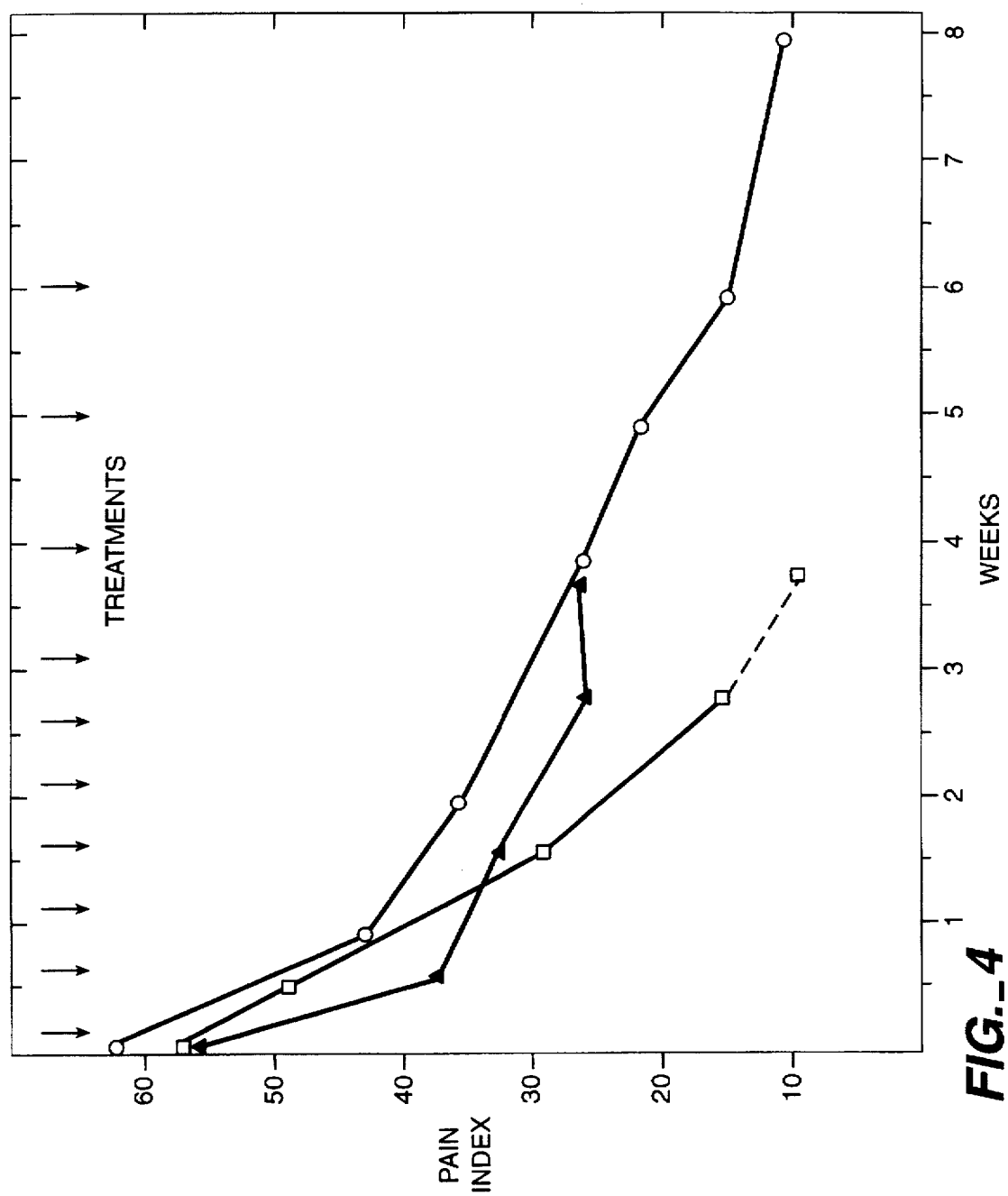
FIG._4

METHOD FOR TREATMENT OF RHEUMATOID ARTHRITIS

The present application is a continuation of Ser. No. 07/878,636, May 5, 1992, abandoned, which is a continuation-in-part of application Ser. No. 07/453,236, Dec. 14, 1989, which was a continuation of application Ser. No. 07/344,463, Nov. 26, 1989, abandoned, which was a continuation of application Ser. No. 06/934,272, filed on Nov. 21, 1986, abandoned.

BACKGROUND OF THE INVENTION

1. Field of the Invention

The present invention relates generally to the treatment of autoimmune disorders by extracorporeal plasma perfusion to remove immunoglobulin and immune complexes. More particularly, the present invention relates to the treatment of rheumatoid arthritis (RA) by continuous or discontinuous plasma perfusion through an immunoadsorbent capable of binding immunoglobulins and immune complexes.

Autoimmune disorders are characterized by the destruction of a patient's body tissues by the patient's own immune system. Severe harm can arise from such a misdirected immune response, causing illness and even death to the patient. Rheumatoid arthritis is an autoimmune disorder of unknown etiology which is characterized by the presence of auto-antibodies.

Rheumatoid arthritis (RA) is a chronic disease which can exhibit a variety of systemic manifestations. This disease has an unknown etiology and characteristically exhibits a persistent inflammatory synovitis which usually involves peripheral joints in a symmetric distribution. Despite the destructive potential of RA, its course can be quite variable. In about two-thirds of patients, a chronic polyarthritis begins insidiously with fatigue, anorexia, generalized weakness and vague musculoskeletal symptoms until the appearance of synovitis becomes apparent. In about 10% of patients, the onset can be more acute with rapid development of polyarthritis. In about one-third of patients, symptoms may initially be confined to one or a few joints. Overall, most patients will experience an intermediate course of the disease. As described above, the potential of the inflammation to cause cartilage destruction, bone erosions and, ultimately, joint deformities is the most important feature of this disease.

Although the etiologic stimulus for RA has not been identified, established rheumatoid synovitis is characterized by persistent immunologic activity. The presence of rheumatoid factor, which is an autoantibody reactive with IgG, suggests that there may be an underlying immune dysfunction in association with RA. This factor was initially described by Waaler in 1940 and later described by Rose and co-workers in 1948. Rheumatoid factors consist of immunoglobulin subclasses IgA, IgG and/or IgM immunoglobulin classes. The idiotypic nature of rheumatoid factor autoantibodies has been described and partially characterized. This suggests that there may be a perturbation in the idiotype/anti-idiotype humoral immune network of patients with rheumatoid arthritis. In addition, the presence of rheumatoid factor can be of prognostic significance because patients with high titers tend to have more severe and progressive disease with extraarticular manifestations. Rheumatoid factor can also be employed to confirm the diagnosis of RA in patients with a clinical presentation of RA and, if at high titer, to designate patients at risk for severe systemic disease. The examination of established rheumatoid synovitis reveals a characteristic constellation of features which include hyperplasia and hypertrophy of the synovial lining cells, focal or segmental vascular changes and infiltration with mononuclear cells often collected into aggregates or follicles around small blood vessels. The predominant infiltrating cell is a T lymphocyte and T4 (helper-inducer) cells predominate over T8 (suppressor-cytotoxic) cells. Evidence of B cell activation can also be found in the inflamed synovium and plasma cells producing immunoglobulin and rheumatoid factor are characteristic features of rheumatoid synovitis. The resultant production of immunoglobulin and rheumatoid factor can lead to the formation of immune complexes with subsequent complement activation and exacerbation of the inflammatory process through the production of anaphylatoxins and chemotactic factors. Indeed, levels of total hemolytic complement, C3 and C4 are markedly diminished in synovial fluid relative to total protein concentration as a result of activation of the classic complement pathway by locally produced immune complexes. All these findings suggest that progression of RA is an immunologically mediated event.

Plasmapheresis, the non-specific removal of a patient's plasma with replacement by normal plasma or plasma expanders, has also been performed on RA patients in attempts to reduce levels of circulating autoantibodies and circulating immune complexes. However, this form of therapy has been generally unsuccessful and is not considered a standard modality for the treatment of RA.

It would therefore be desirable to develop alternate and improved therapies which could provide short- or long-term benefits for RA patients. The therapies should be able to restore the patient's immune status which will help control the misdirected immune response.

2. Description of the Background Art

U.S. Pat. No. 4,681,870, suggests the use of a protein A immunosorbent for the extracorporeal removal of immunoglobulin G (IgG) and immune complexes for the treatment of cancer and autoimmune disorders in general. U.S. Pat. No. 4,685,900, teaches the treatment of a wide variety of diseases based on the removal of "pathological effectors" from the body fluids of a patient, where pathological effectors are defined as "antibodies with reactivity to a self-antigen." While RA is listed as a disease which may be treated, no demonstration of treatment of RA (or any other disease) is provided. Korec et al. (1984) *J. Biol. Resp. Mod.* 3:330–335 and (1986) *Clin. Oncology* 4:210–215 describe the treatment of patients suffering from thrombotic thrombocytopenic purpura by extracorporeal removal of IgG and immune complexes with a polyacrylamide-coated glass bead protein A column. European application 269279 corresponds to great grandparent application 06/934,272. Copending application Ser. No. 07/619,816, describes the treatment of immune thrombocytopenic purpura using a protein A column for extracorporeal plasma perfusion. Terman et al. (1979) Lancet ii:824–826 describes the treatment of a single patient suffering from rheumatoid arthritis by plasma perfusion through a column containing immobilized DNA. The resulting removal of anti-DNA antibodies was found to improve blood characteristics. The full disclosures of each of these references are incorporated herein by reference.

SUMMARY OF THE INVENTION

The present invention provides a method for treatment of patients suffering from rheumatoid arthritis (RA). The present invention relies on the non-discriminate removal of immunoglobulin, particularly IgG, and immune complexes, particularly those containing IgG. By non-discriminate removal, it is meant that the immunoglobulin and immune complexes are removed regardless of their binding specificity. Usually, the immunoglobulin and immune complexes will be extracorporeally removed by contact with an immunoadsorbent capable of binding to a constant region of the immunoglobulin to achieve the desired non-discriminate removal.

In a preferred embodiment, the immunoglobulin and immune complexes will be removed by extracorporeal contact with a protein A immunoadsorbent. Protein A is a bacterial cell wall protein derived from Staphylococcus which binds IgG and IgG-containing immune complexes, where the binding affinity to the immune complexes is higher than for the free immunoglobulin. Using the protein A immunoadsorbents, effective treatment of patient's suffering from RA has been demonstrated.

BRIEF DESCRIPTION OF THE DRAWINGS

FIG. 1 is an exploded view of an immunoadsorbent column useful for performing the method of the present invention.

FIG. 2 is a diagrammatic representation of a system using the immunoadsorbent column of FIG. 1 for continuous mode extracorporeal removal of immunoglobulin and immune complexes according to the method of the present invention.

FIGS. 3 and 4 illustrate the reduction in the average pain and swelling indices, respectively, for three patients treated by the method of the present invention.

DESCRIPTION OF THE PREFERRED EMBODIMENT

Rheumatoid arthritis (RA) is treated by the non-discriminate removal of immunoglobulin G (IgG) and immune complexes containing IgG from a patient's blood. It has been found that such removal produces an immune modulation that results in a lowering of the titer of rheumatoid factor antibodies and reduces or eliminates episodes of RA disease activity. By non-discriminate removal, it is meant that IgG and IgG-containing immune complexes are removed regardless of the specificity or idiotype of the immunoglobulin. This is achieved by binding and removing the IgG and IgG-containing immune complexes through the constant region in such molecules and complexes. Preferred treatment modalities utilize protein A immunoadsorbents which bind to IgG-containing immune complexes with particularly high affinities.

The methods of the present invention utilize an immunoadsorbent column having an immunoadsorbent material therein which is suitable for the extracorporeal treatment of a patient's plasma to remove IgG and IgG-complexes therefrom. The extracorporeal treatment may be provided by continuously removing a patient's blood, separating the blood cells therefrom, treating the blood plasma in the immunoadsorbent column to remove the IgG and IgG-complexes, and mixing and returning the treated plasma and blood cells directly to the patient. Alternatively, after the blood has been removed and the blood cells separated, the blood cells may be directly reinfused into the patient. The separated plasma may be collected, treated in the immunoadsorbent column of the present invention, again collected and then returned to the patient at a later time.

Suitable immunoadsorbent materials comprise receptors bound to a solid phase matrix, where the receptors are capable of specifically (but non-discriminantly) binding immunoglobulin, and immune complexes. Useful receptors include these which bind to the constant region of IgG, such as protein A, anti-Ig antibodies, Clq, rheumatoid factor, conglutinin and the like. The preferred novel immunoadsorbent material of the present invention comprises protein A covalently coupled to a solid-phase silica matrix under particular conditions which have been found to maximize activity of the protein A and binding capacity of the column while minimizing leakage of the protein A and other substances from the column during use.

The immunoadsorbent material of the present invention will have a binding capacity of at least 5 mg IgG/gm adsorbent, usually 7 mg/gm or greater. The immunoadsorbent system of the present invention allows removal of up to about 750 to 1500 mg of the circulating IgG and IgG-complexes, usually about 1000 mg by treatment of the plasma. Usually, no more than 1 g of antibody and circulating IgG-complexes will be removed in any given treatment (i.e., one adsorption using a treatment column as described in detail below).

Protein A is a cell surface protein which is isolated from particular strains of Staphylococcus and able to bind free IgG and IgG-complexes. IgG-complexes are antigen-IgG complexes which circulate in patient serum and are not removed by the normal phagocytic mechanisms of the immune system.

Protein A may be obtained from cultures of *Staphylococcus aureus*, for example *S. aureus* Cowan I, by harvesting the cells and lysing with a suitable lytic agent, such as lysostaphin. The protein A may then be purified by any suitable technique, such as ion exchange combined with molecular sieve chromatography, to a final purity of 90–99%, usually about 95%. A preferred purification technique is described in U.S. Pat. No. 5,037,649, the full disclosure of which is incorporated herein by reference. Protein A may also be obtained by expression of recombinant vectors in other bacterial hosts, as taught in U.S. Pat. No. 4,617,266, as well as by a variety of other techniques. Alternatively, suitably purified protein A may be obtained from a number of commercial suppliers, such as IMRE Corporation, Seattle, Wash.

The solid phase matrix will usually comprise inert particles, such as silica particles, glass beads, polymeric beads, agarose gels, cross-linked dextrans, and the like. Solid-phase silica matrices are preferred and may comprise virtually any form of particulate silica including amorphous silicas, such as colloidal silica, silica gels, precipitated silicas, and fumed silicas; microcrystalline silicas such as diatomites; and crystalline silicas such as quartz. The silica should have a particle size in the range from about 45 to 120 mesh, usually in the range from 45 to 60 mesh.

In the preferred embodiment, the solid-phase matrix of the immunoadsorbent material will be formed from diatomite aggregates. The diatomite material will be cleaned to remove any remaining organic material and the surface of the aggregates may be hardened in order to lessen breakage and degradation of the immunoadsorbent during use. The diatomite material will consist primarily of silica (silicon dioxide) with lesser amounts of other minerals, including aluminum oxide, calcium oxide, magnesium oxide, ferric oxide, and the like. Usually, the diatomite material will comprise at least 80% silica, with less than 5% by weight of any other mineral. Other impurities may be present in the diatomite, but care should be taken that such impurities are non-toxic and non-degradative to the biological fluid being treated. A particularly suitable solid-phase silica (diatomite) matrix may be obtained from JohnsManville Corporation under the tradename Chromosorb®.

The protein A is covalently coupled to the solid-phase silica matrix by derivatizing the matrix to introduce active reactive functional groups, and reacting the derivatized matrix with a coupling agent or under chemical conditions which binds the protein A to the matrix. Exemplary protocols for such binding are as follows.

Amino groups may be introduced to the silica matrix as the reactive functional group by any suitable method. For example, the silica matrix is first acid washed, followed by extensive rinsing with water and drying. The acid washed silica is then reacted in a 5% to 10% solution of an aminosilane, such as γ-amino-propyltriethoxysilane, with the pH adjusted to about 3.0. After 2 hours at about 75° C., the silica matrix is again washed extensively with water and dried overnight at 100° C.

Carboxyl groups may be introduced to the silica matrix as the reactive functional group by further reacting the amino-derivatized material, as just described, with succinic anhydride as follows. The silica matrix is mixed with succinic anhydride in a suitable buffer, such as 0.5M phosphate buffer, and the pH adjusted to about 6.0. After 12 to 16 hours at room temperature, the silica matrix is extensively washed, and dried.

Hydroxyl groups (in addition to those hydroxyl groups occurring in the native structure of the matrix) may be introduced to the silica matrix by any suitable method. For example, the silica matrix is first acid washed, rinsed extensively with water, and dried. The acid washed silica is then reacted in a 5-10% solution of a silane such as γ-glycidoxypropyltrimethoxysilane. After a 2 hour incubation at 75° C., the silica matrix is again washed extensively with water and dried at 100° C.

Once the silica matrix has been derivatized with either amino and/or carboxyl groups, the protein A is introduced by reaction with a carbodiimide which forms a covalent link between the matrix and the protein A. The carbodiimide will have the formula:

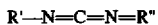

where R' and R" may be the same or different, being either alkyl, substituted-alkyl, benzyl, substitutedbenzyl, or hydrogen. Alkyl or substituted-alkyl may be straight, branched or cyclic, and R will usually have fewer than 12 atoms, and six or fewer heteroatoms (i.e., other than carbon and hydrogen). If substituted-benzyl, R will usually have three or fewer substitutions which will typically be halogen atoms. Suitable carbodiimides are well known in the art. The preferred carbodiimide is 1-cyclohexyl-3-(2-morpholionoethyl) carbodiimide metho-p-toluenesulfonate.

The binding reaction for the amino-derivatized matrix is carried out under the following conditions. The protein A is mixed in water in the presence of the carbodiimide. The pH of the solution is adjusted to the range from 3.5 to 4.5, usually about 4.5, and the silica matrix is introduced and gently mixed for an extended period, usually about 20 to 25 hours at room temperature. The matrix is then extensively washed with water, dried, and acid washed at a pH from about 2.0 to 2.5, usually about 2.25, to remove labile protein and other substances which are non-covalently bound to the silica matrix. The material is then finally washed, dried and checked for the presence of pyrogens. Suitable test for the presence of pyrogens are commercially available.

The binding process for the carboxylderivatized silica matrix is as follows. A carbodiimide (as above) is dissolved in water, and the solution is adjusted to a pH in the range from 3.5 to 4.5, usually about 4.5 pH. After introducing the silica matrix, the solution is gently mixed for an extended period, usually about 10 to 25 hours, more usually about 12 to 20 hours, at room temperature. The silica matrix is then removed and extensively washed with water. The protein A is then dissolved in water, the pH adjusted to the range from 3.5 to 4.5, usually about 4.5, and the silica matrix added and mixed for about 15 to 30 hours, usually about 20 to 25 hours at room temperature. The silica matrix is then extensively washed with water, dried, and washed in an acid wash (pH 2.0 to 2.5, usually about 2.25) to remove non-covalently bound protein A and other substances. The silica matrix is then washed a final time, and checked for pyrogens.

The binding process for the hydroxyl derivatized silica matrix is as follows. Cyanogen bromide is dissolved in water. The silica matrix is added to water and the pH is adjusted to 11.0. The cyanogen bromide solution is added to the silica matrix, the mixture is constantly stirred keeping the silica particles in suspension, and the pH is maintained between 11.0 and 11.5 by addition of NaOH until pH stabilization occurs. The activated silica matrix is extensively washed with water, mixed with a solution of protein A with the pH adjusted to 8.5–9.0, and mixed overnight at 25° C. After coupling, the matrix is washed extensively with water, dried, and washedB in an acid wash, pH 2.5, to remove non-covalently bound and acid labile protein A linkages. The silica matrix is washed a final time and checked for pyrogens.

The pH range of from 3.5 to 4.5 for binding of the protein A to the amino and/or carboxyl functional groups on the silica matrix and the pH range of 8.5 to 9.0 for binding of the protein A to the hydroxyl functional groups are both important. The efficiency of binding and the retained activity of the protein A both diminish as the pH deviates outside of these narrow ranges. Moreover, it has been found that a mild acid wash with a pH in the range from about 2.0 to 2.5 successfully removes non-covalently bound substances from the silica matrix, particularly cleaving labile protein A linkages. The acid treatment is thus important in achieving a stable immunoadsorbent material which is able to retain the IgG and IgG-complexes bound within the column and avoid loss of protein A into the plasma being treated.

Referring now to FIG. 1, the construction of a suitable cartridge 10 for containing the immunoadsorbent material as just described is illustrated. The cartridge comprises a cylinder 12, a pair of retaining screens 14, and a pair of end caps 16. The end caps 16 each include a flange element 18 projection from one surface thereof and a connector nipple 20 projecting from the other surface thereof. The connector nipple includes an axial passage 22 therethrough to define inlet/outlet ports through the end caps 16.

The cylinder 12 includes an annular groove 26 at each end thereof. The flange element 18 on each end cap includes a mating ring 28 on the inner cylindrical surface thereof, which mating ring engages the annular groove 26 when the caps are placed over the end of the cylinder 12. Each screen 14 includes a gasket 30 around its circumference, which gasket serves as sealing member between the end cap 16 and the cylinder 12 when the cartridge 10 is assembled. To assemble the cartridge 10, a first screen 14 is placed over one end of the cylinder 12, and an end cap 16 is fitted over the screen 14. The cylinder 12 is then filled with the immunoadsorbent material as described above, and assembly of the cartridge completed by placing the remaining screen 14 and end cap 16 in place.

The dimensions of the cartridge 10 are not critical, and will depend on the desired volume of immunoadsorbent material. The volume of the cylinder 12 will typically range from about 50 to 500 cc, having a diameter in the range from about 4 to 8 cm and a length in the range from about 5 to 10 cm.

A column 11 (FIG. 2) which comprises a cartridge 10 containing a suitable amount of the immunoadsorbent material prepared as described above, may be sterilized, typically with a gas sterilant such as ethylene oxide, and either used immediately or sealed and stored for later use.

Treatment protocols may be performed with the column 11 as follows. Prior to use, the column 11 will be washed with normal saline followed by a wash with normal saline containing heparin or other suitable anti-coagulant such as anti-coagulant citrate dextrose (ACD). The column 11 may then be connected to a cell separator 40 (FIG. 2) to receive separated plasma therefrom. The cell separator 40 may be a continuous flow cell separator, such as an IBM Model 2997, available from COBE, Golden, Colo., or may comprise a semi-permeable membrane which allows passage of the plasma and blood proteins, but prevents passage of the cellular elements of the blood. In the case of a semi-permeable membrane, a blood pump 42 will be required to pass the blood through the membrane. Suitable blood pumps include a tube and peristaltic pumps where the blood is isolated from the pumping machinery to prevent contamination. The blood will pass through the cell separator 40 at a rate in the range from about 10 to 20 ml/min typically until a total volume of about 2 liters of blood has been passed. The blood cells are mixed with the plasma passing from the treatment column 11, and the recombined blood returned to the patient. Typically, a microfilter 44 is provided at the outlet of the treatment column 11 to prevent passage of macroscopic particles which might be lost from the column 11.

Individual treatment protocols employing the immunoadsorbent column of the present invention may be performed by an on-line (continuous) protocol where a patient's blood is continuously drawn and separated into plasma and cellular components. While the blood is continuing to be drawn, the plasma is contacted with the immunoadsorbent and the plasma and cellular components are reinfused into the patient. Such an on-line protocol allows relatively large volumes of plasma in the range from about 300 to 3000 ml to be treated.

Alternatively, off-line (discontinuous) treatment protocols may also be employed where a discrete volume of blood is drawn, usually in the range from about 200 to 600 ml, by conventional phlebotomy. The blood is then separated into plasma and cellular components, and then cellular components substantially immediately reinfused into the patient. The plasma is separately treated with the immunoadsorbent and reinfused to the patient some time later, usually from several hours to several days later. Multiple volumes of blood, e.g., two, three, or four volumes within the above range, may be treated at any one session, with the cellular components and treated plasma being returned to the patient prior to drawing the next blood volume.

The method of the present invention is used to treat patients suffering from clinical symptoms of RA, particularly those patients having elevated titers of rheumatoid factor antibodies. The method comprises the extracorporeal treatment of the patient's blood producing an immune modulation that reduces the titer of rheumatoid factor, as well as the levels of IgG-containing immune complexes in the patient's blood. This is achieved by employing the immunoadsorbent system of the present invention which allows for removal of up to about 750 to 1500 mg of circulating IgG and IgG containing complexes, usually about 1000 mg by treatment of the plasma.

To achieve and maintain the above-stated immune modulation, it will be necessary to periodically treat a patient's blood according to the individual treatment protocols described above. Usually, the treatments will be performed at a frequency of at least about once each week, preferably from about once to four times per week, and usually from about two to three times per week. Treatments at such frequency may be continued indefinitely, or may consist of a discrete number of treatments, for example in the range from about 6 to 12. In some cases, it may be desirable to perform a series of treatments over a number of weeks, followed by a period where no treatments are performed for a number of weeks, followed again by a treatment period.

The following examples are offered by way of illustration and not by way of limitation.

EXPERIMENTAL

1. Preparation of Immunoadsorbent Material

Acid washed silica matrix (Chromosorb® P, No. C5889, Johns-Manville, 1.25 kilograms) was weighted out, divided into 4 parts, and added to four Fernback type flasks. The matrix was re-hydrated with water and vigorously shaken overnight in a gyrator shaker at approximately 150 rpm. After this procedure, the silica matrix was extensively washed with water to remove generated fine particles. This procedure appeared to make the shape of the silica matrix particles more uniform resulting in matrix particles which generate few fines in later handling procedures. After washing, the silica matrix was added to an approximately 5–10% solution of appropriate silane, incubated for 2 hours at 75° C., extensively washed with water, and baked dry at 115° C.

The dried silizanized silica matrix (1 kilogram) was re-hydrated and extensively washed with water to remove generated fines. The silica matrix was then mixed with 2 grams of protein A and 50 grams of carbodiimide (1-cyclohexyl-3-(2-morpholinoethyl) carbodiimide metho-p-toluenesulfonate) and the pH of the mixture adjusted to 4.5.

The mixture was gently rotated on a roller apparatus for 22 hours at 25° C. The silica matrix was then extensively washed with water, dried at 37° C., and the uptake of protein A was determined. After drying, 3 liters of acid water, pH 2.5, was added to the silica matrix, incubated for 5 minutes at 25° C., and the amount of protein A released from the matrix was determined. The matrix was extensively washed with water, dried, and the amount of protein A per gram of silica was determined. The results were as follows:

| Bound Protein A | 1966 mg |
| Protein A released | 440 mg |
| Protein A/gm adsorbent | 1.5 mg |

2. Use of Immunoadsorbent to Separate IgG and IgG Complexes from Normal Human Serum Immunoadsorbent prepared as described above was incubated with 2 ml of normal human serum for 5 minutes at 25° C. After incubation, the silica matrix was washed with 100 ml of phosphate buffered saline (PBS), pH 7.5. Bound proteins were eluted with 12.5 ml of PBS, pH 2.5, and neutralized to pH 7.5. The total protein eluted was determined to be approximately 10 mg, using the procedure as described by Lowry et al. (1951) *J. Biol. Chem.* 193:265–272. The eluted protein was subjected to polyacrylamide gel electrophoresis, and prominent bands were detected at 50 kD and 25 kD, corresponding to the heavy and light chains of IgG, respectively. The presence of IgG was confirmed by double immunodiffusion analysis employing E-chain specific anti-human IgG.

To determine removal of IgG complexes by the immunoadsorbent, 2.5 ml of normal human serum was incubated with heat-aggregated human IgG to fix complement to the aggregates. This combination behaves as immune complexed IgG. Immunoadsorbent prepared as described above was incubated with 0.8 ml of the heat-aggregated serum for 5 minutes at 25° C. This was repeated 3 times until a total volume of 2.5 ml was passed through the immunoadsorbent, and fractions were collected until all the serum was passed through the immunoadsorbent. IgG immune complexes in pre- and post-perfusion serum fractions were measured employing the Raji cell binding IgG immune complex assay as described by Theofilopoulos et al. (1974) J. Exp. Med. 140:1230–1244. The results are presented in Table 1.

TABLE 1

| Sample* | Immune Complex (μg/ml) | % Reduction |
|---|---|---|
| Pre-perfusion | 160 | — |
| Post-perfusion - | | |
| Fraction 1 | 120 | 25 |
| Fraction 2 | 125 | 22 |
| Fraction 3 | 105 | 34 |
| Fraction 4 | 104 | 35 |

*Equivalent protein quantities were assayed to control for dilutional effects.

As shown in Table 1, immune complex levels of the serum were reduced by passage through the immunoadsorbent.

3. Therapeutic Use of Column To Treat RA

Three patients with RA were treated with plasma perfusion over protein A columns prepared as described above. The changes that occurred in the clinical parameters are reported below.

Three patients were diagnosed with RA. Extracorporeal immunoadsorption procedures were performed employing a continuous flolw plasma-cell separator system. The cellular components were returned unprocessed and plasmaswas perfused over a column containing 200 mg protein A covalently bound to silica prepared as described above, and returned to the patient. The protein A was isolated from pure cultures of Staphylococcus aureus. Protein A purity was determined by polyacrylamide gel electrophoresis, and IgG binding capacity was determined. The protein A was covalently coupled to silica, loaded into a biocompatible cartridge, and sterilized by exposure to ethylene oxide. sterility was confirmed employing strips impregnated with spores of Bacillus subtilis (Raven Biological Laboratory, Omaha, Nebr.). In addition, studies revealed that extensive washing of the column with 4L of sterile, pyrogen-free water, immediately prior to use, resulted in a lack of detectable pyrogens (Limulus amoebocyte lysate test, associates of Cape Cod, Woods Hole, Mass.) Each protein A treatment column had the capacity to bind approximately 1 gram of IgG from plasma. Plasma flow rates were between 10 to 20 ml/min. Three hundred mls to 2 liters of plasma were perfused during each procedure. Fifteen treatments were performed over a 12 week period.

RESULTS

No major complications occurred during the treatment procedures and, overall, all treatments were well tolerated. During the treatment period, several inflammed joints were evaluated for pain and swelling. In all three RA patients, joint pain and joint swelling decreased during the treatment period. The changes in joint pain and join swelling for the three RA patients are depicted in FIGS. 3 and 4. Note the significant decreases in both indexes during the treatment period indicative of clinical improvement.

Although the foregoing invention has been described in detail for purposes of clarity of understanding, it will be obvious that certain modifications may be practiced within the scope of the appended claims.

What is claimed is:

1. A method for treating a patient suffering from rheumatoid arthritis, consisting essentially of
   (A) removing blood from the patient and separating cellular components therefrom to provide a cellular-component volume and a plasma volume,
   (B) contacting the plasma volume with an immunoadsorbent to effect removal of immunoglobulin G and immune complexes, wherein the immunoadsorbent comprises an inert carrier and protein A bound thereto, and then
   (C) mixing and returning directly to the patient the cellular-component volume and the immunoadsorbent-treated plasma volume from step (B), wherein step (C) is effected while step (A) is still being carried out.

2. The method of claim 1, wherein the plasma volume in step (B) is contacted with an immunoadsorbent comprising silica and protein A bound thereto.

3. The method of claim 1, wherein the plasma volume in step (B) is contacted with an immunoadsorbent having a binding capacity, for immunoglobulin G and immune complexes, such that up to about 750 mg of immunoglobulin G and immune complexes are removed from the plasma volume.

4. The method of claim 1, wherein the plasma volume in step (B) is contacted with an immunoadsorbent having a binding capacity, for immunoglobulin G and immune complexes, such that up to 1500 mg of immunoglobulin G and immune complexes are removed from the plasma volume.

5. The method of claim 1, wherein about 1000 mg of immunoglobulin G and immune complexes are removed from the plasma volume.

6. The method of claim 1 wherein the protein A is covalently bound to the inert carrier.

7. The method of claim 1 wherein about 300 ml to about 3000 ml of the patient's plasma is contacted with said immunoadsorbent and infused into said patient.

8. The method of claim 1 wherein the preparation of the plasma volume and cellular component volume, the contacting with the immunoadsorbent, and the infusing are repeated at a frequency of about one time to four times per week until the patient's condition improves.

9. The method of claim 8 wherein each step is repeated one time per week.

10. The method of claim 8 wherein each step is repeated about 6 to 12 times over a first treatment period, followed by a period of no treatments, which is followed by at least a second treatment period wherein each step is repeated about one time to four times per week for about 6 to 12 treatments.

11. The method of claim 10 wherein the sequence is repeated until the patient's condition improves.

12. The method of claim 1 wherein each step is repeated indefinitely at a frequency of about one time to four times per week.

13. The method of claim 1, wherein the plasma is obtained from about 200 ml to 600 ml of the patient's blood.

* * * * *